United States Patent [19]

Fushimi et al.

[11] Patent Number: 5,334,794
[45] Date of Patent: Aug. 2, 1994

[54] PROCESS FOR PRODUCING MONOALKENYL AROMATIC HYDROCARBON COMPOUND

[75] Inventors: Norio Fushimi; Ko Kedo; Kenji Inamasa; Makoto Takagawa, all of Tsukuba, Japan

[73] Assignee: Mitsubishi Gas Chemical Company, Inc., Tokyo, Japan

[21] Appl. No.: 47,811

[22] Filed: Apr. 15, 1993

[30] Foreign Application Priority Data

Jun. 22, 1992 [JP] Japan .................. 4-162692

[51] Int. Cl.$^5$ .............................. C07C 2/72
[52] U.S. Cl. ...................... 585/452; 585/435; 585/438; 585/467
[58] Field of Search ............. 585/435, 438, 452, 467

[56] References Cited

U.S. PATENT DOCUMENTS

| | | | |
|---|---|---|---|
| 3,244,758 | 4/1966 | Eberhardt | 260/668 |
| 3,839,485 | 10/1994 | Wrisberg et al. | 260/683 R |
| 4,977,124 | 12/1990 | Smith | 502/174 |

FOREIGN PATENT DOCUMENTS 2063174 7/1971 Fed. Rep. of Germany .
WO91/16284 10/1991 PCT Int'l Appl. .

*Primary Examiner*—Asok Pal
*Assistant Examiner*—P. Achutamurthy
*Attorney, Agent, or Firm*—Frishauf, Holtz, Goodman & Woodward

[57] ABSTRACT

A process for producing a monoalkenyl aromatic hydrocarbon compound which comprises alkenylating a side chain of an aromatic hydrocarbon compound having at least one hydrogen atom bonded at an α-position of the side chain (such as xylene) with a conjugated diene having 4 or 5 carbon atoms (such as butadiene) in the presence of a catalyst comprising a mixture obtained by heat treating metallic sodium together with a mixture of a zirconium oxide and a potassium compound in an inert gas atmosphere. An industrially useful monoalkenyl aromatic hydrocarbon compound is produced in a high yield at a low cost with enhanced safety from a specific aromatic hydrocarbon compound and a specific conjugated diene compound.

15 Claims, No Drawings

PROCESS FOR PRODUCING MONOALKENYL AROMATIC HYDROCARBON COMPOUND

BACKGROUND OF THE INVENTION

1. Field of the Invention

The present invention relates to a process for producing a monoalkenyl aromatic hydrocarbon compound. More particularly, it pertains to a process for producing a monoalkenyl aromatic hydrocarbon compound by subjecting an aromatic hydrocarbon compound to side-chain alkenylation with a conjugated diene having 4 or 5 carbon atoms.

2. Description of Related Arts

As a process for producing a monoalkenyl aromatic hydrocarbon compound by subjecting an aromatic hydrocarbon compound to side-chain alkenylation with a conjugated diene having 4 or 5 carbon atoms, there is known the process in which is employed as a catalyst an alkali metal such as sodium and potassium or an alloy thereof.

For example, German Patent No. 557514 discloses the use of metallic sodium as a catalyst in the above-mentioned process and Eberhardt et al. describes the use of metallic sodium supported on an alkaline earth metal oxide as a catalyst in J. Org. Chem., vol. 30 (1965), pp 82 to 84.

Likewise, there are disclosed the use of metallic potassium in Japanese Patent Publication No. 17937/1975, the use of a potassium/sodium alloy or a mixture of metallic potassium and metallic sodium in Japanese Patent Publication Nos. 17975/1975 and 8930/1976, and the use of metallic potassium supported on an alkali metal oxide or an alkaline earth metal oxide in U.S. Pat. No. 3244758 and the aforementioned J. Org. Chem., vol. 30 (1965), pp 82 to 84, each as the catalyst in the above-mentioned process.

There is also disclosed the use of the mixture obtained by heat treating a potassium compound and metallic sodium at 300° C. or a temperature not lower than 350° C. as the catalyst in the above-mentioned process in Japanese Patent Application Laid-Open Nos. 27929/1972 and 31935/1972.

Among the aforestated processes, the process in which is used as a catalyst metallic sodium with or without being supported on an alkaline earth metal oxide is impractical because of insufficiency in both catalytic activity and selectivity of reaction. The process in which is used as a catalyst, metallic potassium, a potassium/sodium alloy or a mixture of metallic potassium and metallic sodium exhibits a high catalytic activity but causes violent reaction of the catalyst with oxygen, moisture and the like. Therefore, an attempt to put the aforesaid process into industrial practice involves various problems concerning safety due to possible hazards such as fire and explosion in addition to the economic problem in that metallic potassium is expensive as compared with metallic sodium.

On the other hand, the process in which is used as a catalyst the mixture obtained by heat treating a potassium compound and metallic sodium at a high temperature is characterized in that metallic potassium or a potassium alloy is not directly employed, but can not be said to be necessarily practical because of insufficient catalytic activity and the necessity for treating the highly inflammable powder at a high temperature.

Under such circumstances, intensive research and investigation were made by the present inventors in order to solve the above-described problems. As a result, it has been found by the present inventors that a monoalkenyl aromatic hydrocarbon compound can be produced in high reaction performance at a low cost by the process with high safety which comprises employing a solid base-catalyst obtained by heat treating a zirconium oxide containing a potassium compound together with metallic sodium in the atmosphere of an inert gas at the melting point of sodium or higher. The present invention has been accomplished on the basis of the above-mentioned finding.

SUMMARY OF THE INVENTION

It is an object of the present invention to provide a process with safety for producing a monoalkenyl aromatic hydrocarbon compound in high yield at a low cost by eliminating the aforestated disadvantages in subjecting an aromatic hydrocarbon compound to side-chain alkenylation with a conjugated diene having 4 or 5 carbon atoms.

It is another object of the present invention to provide a catalyst for producing a monoalkenyl aromatic hydrocarbon compound in high yield at a low cost.

Other objects of the present invention will be obvious from the description of this text hereinafter disclosed.

Specifically, the present invention provides a process for producing a monoalkenyl aromatic hydrocarbon compound which comprises alkenylating a side chain of an aromatic hydrocarbon compound having at least one hydrogen atom bonded at an $\alpha$-position of the side chain with a conjugated diene having 4 or 5 carbon atoms in the presence of a catalyst comprising the mixture obtained by heat treating metallic sodium together with a zirconium oxide containing a potassium compound in the atmosphere of an inert gas.

DESCRIPTION OF PREFERRED EMBODIMENTS

Examples of the specific aromatic hydrocarbon compound having at least one hydrogen atom bonded at an $\alpha$-position of the side chain to be employed as the starting raw material in the present invention include monocyclic aromatic hydrocarbons such as monoalkylbenzenes enumerated by toluene; ethylbenzene; n-propylbenzene; isopropylbenzene; n-butylbenzene; secbutylbenzene; and isobutylbenzene, dialkylbenzenes enumerated by o-, m- and p-xylene; o-, m- and p-ethyltoluenes; and o-, m- and p-diethylbenzenes, trialkylbenzenes enumerated by mesitylene; and pseudocumene and polyalkylbenzenes enumerated by 1,2,3,5-tetramethylbenzene; 1,2,4,5-tetramethylbenzene; pentamethylbenzene; and hexamethylbenzene, and polycylic aromatic hydrocarbons such as 1- and 2-methylnaphthalene, dimethylnaphthalenes, tetrahydronaphthalenes (e.g., alkyltetrahydronaphthalene) and indanes (e.g., alkylindane).

As the conjugated dienes having 4 or 5 carbon atoms as another starting raw material, there are preferably used 1,3-butadiene; 1,3-pentadiene; and isoprene.

Examples of the potassium compound to be employed for preparing the catalyst in the present invention include halogenides, sulfates, nitrates, phosphates, carbonates, hydroxides, carboxylates and zirconares each of potassium, specifically exemplified by potassium fluoride, potassium chloride, potassium bromide, potassium iodide, potassium sulfate, potassium nitrate, potassium phosphate, potassium monohydrogenphosphate, potassium dihydrogenphosphate, potassium carbonate, potassium hydrogencarbonate, potassium hydroxide, potassium formate, potassium acetate and potassium zirconate, among which are particularly desirable potassium hydroxide, potassium carbonate, potassium hydrogencarbonate and potassium zirconate.

The above-mentioned potassium compound may be used alone or as a mixture with at least one other potassium compound. The potassium compound, even when incorporated with other alkali metals such as cesium, sodium and lithium in an almost equivalent weight, may be used without any problem insofar as the aforesaid potassium compound is present in a prescribed amount.

The zirconium oxide containing a potassium compound may be prepared by either a wet system or a dry system provided that the above two compounds are mixed with and dispersed in each other. For the purpose of a particularly homogeneous dispersion, however, a wet system is preferable. In the case of preparing the mixture by dry system, the above two compounds may be mixed in the form of powder. When there is used a comparatively low melting potassium compound such as potassium hydroxide, the process is adoptable in which the compounds are mixed with heating at a temperature higher than the melting point of the potassium compound for the homogenous dispersion. As the process for preparing the mixture by a wet system, there is available the process wherein a zirconium oxide is impregnated or kneaded with an aqueous solution of a potassium compound, followed by drying, calcination and/or firing. In the case where the compounds are treated by drying, calcination and/or firing after mixing the compounds, the zirconium is not necessarily required to be in an oxide state at the time of preparing the mixture but may be in a precursor state which is convertible into the oxide thereof by means of drying, calcination and/or firing. Examples of such compound in a precursor state include an oxy-zirconium compound such as zirconium oxycarbonate and zirconium oxyacetate and zirconium hydroxide. The above-mentioned calcination and/or firing are carried out at a temperature of 300° to 700° C., preferably 350° to 600° C.

The mixing ratio by parts by weight of the potassium compound to the zirconium oxide is 0.01 to 5, preferably 0.02 to 2 in terms of metallic potassium. A mixing ratio thereof less than the above lower limit results in such disadvantage that side reaction such as the isomerization of the alkenyl aromatic hydrocarbon compound to be produced is likely to occur, catalytic activity is likely to be deteriorated, and an unreasonably large amount of the catalyst is required to maintain a high catalytic activity, thus complicating the post-treatment after the reaction, whereas a mixing ratio thereof more than the above higher limit unfavorably makes it difficult to manifest the effect due to the use of the zirconium oxide, for example, a long time required to obtain the highly active catalyst and the necessity for heat treatment at a higher temperature.

The preparation of the catalyst by mixing the zirconium oxide containing a potassium compound with metallic sodium is carried out by mixing with heating the compounds in the atmosphere of an inert gas usually at a temperature not lower than 97.8° C., that is the melting point of metallic sodium. By the term "inert gas" as mentioned herein is meant a gas that is substantially non-reactive with the catalyst to be prepared under the preparation conditions for the catalyst, which inert gas is exemplified by nitrogen, helium and argon.

The catalyst to be used in the present invention is prepared at a temperature in the range of desirably 97.8° to 500° C., more desirably 97.8° to 300° C. The heating treatment time is usually ranging from 5 to 300 minutes. An catalyst preparation temperature lower than 97.8° C. results in difficulty in homogeneously dispersing metallic sodium in the zirconium oxide containing a potassium compound and in bringing metallic sodium into effective contact with the above oxide because of the infusibility of metallic sodium at a temperature lower than 97.8° C., thereby requiring a long preparation time and rendering itself impractical. On the other hand, although the catalyst can be prepared at a temperature exceeding 500° C., it can not be said that handling of an inflammable substance at a high temperature is favorable in industrial practice.

The ratio of metallic sodium to the potassium compound is 0.01 to 10, preferably 0.02 to 5 in terms of the atomic ratio of metallic sodium to metallic potassium in the potassium compound. A ratio outside the above-mentioned range unfavorably results in failure to sufficiently exert the effect due to the use of metallic sodium and the potassium compound, thereby necessitating an unreasonably large amount of the catalyst to assure the required catalytic activity.

In employing the catalyst according to the present invention thus obtained in the alkenylation reaction, various reaction systems are available and exemplified by a batchwise or a semi-batchwise system in which the starting raw material is fed batchwise or semi-batchwise into a reactor which has previously been fed with the catalyst; a complete mixing system in which the catalyst and starting raw material are continuously fed into a reactor; and a flow system through a fixed bed in which the starting raw material is allowed to flow through a reactor which has previously been packed with the catalyst. The reaction system should be selected in accordance with the type of the objective reaction product. In general, the selectivity to the objective monoalkenyl aromatic hydrocarbon compound can be enhanced by the system wherein an aromatic hydrocarbon as one of the starting raw materials is allowed to be present in excess against a conjugated diene. For the purpose of enhancing the selecticity, a semi-batchwise system is preferable in which a conjugated diene is continuously fed into the reaction system. In the case of continuous reaction by a complete mixing system or a flow system through a fixed bed, it is preferable for enhancing the selectivity to adopt the reaction system capable of lowering the concentration of a conjugated diane in the reactor such as the system in which a conjugated diane is fed into each stage of a multistage reactor to be adopted.

The reaction temperature in the process according to the present invention is in the range of 50° to 300° C., preferably 90° to 200° C. A temperature lower than the above lower limit can cause the reaction to take place, but results in failure to attain a sufficient reaction rate; and besides tends to lower the selectivity, while that higher than the above higher limit unfavorably leads to an increased amount of byproduct such as tar components.

The reaction pressure is in the range of 0.05 to 50, preferably 0.1 to 20 absolute atmospheric pressure.

In the process according to the present invention, the molar ratio of the conjugated diane having 4 or 5 carbon atoms as a starting raw material to the aromatic hydrocarbon as another starting raw material is generally 0.01 to one (1), preferably 0.03 to 0.5. A molar ratio thereof higher than the above higher limit unfavorably causes remarkable side reactions such as polymerization and an increase in the formation of the compound in which the monoalkenyl aromatic hydrocarbon compound thus produced is further reacted with the excess diene to allow the addition of at least two molecules of the diene to one molecule of the aromatic hydrocarbon, whereby the selectivity to the objective compound is undesirably worsened.

The amount of the catalyst to be used in the process according to the present invention is 0.01% or more, preferably 0.05% or more by weight based on the amount of the aromatic hydrocarbon as a starting raw material.

As described hereinbefore, the reaction system is selected from a batchwise system, a semi-batchwise system, a complete mixed flow system and the like in putting the process of the invention into practice. There is usually adopted a reaction time or a retention time in a complete mixing system of 0.1 to 10 hours. In the case of a flow system through fixed bed, liquid hourly space velocity (LHSV) for the aromatic hydrocarbon in the range of 0.1 to 10 $h^{-1}$ is usually selected.

In the case of carrying out the reaction with a suspended catalyst, the separation of the reaction liquid from the catalyst after the reaction can be easily performed by any of the conventional methods including sedimentation, centrifugal separation and filtration. The separated catalyst may be circulated through the reaction system or subjected to the necessary step such as removing organic substances attached thereto by combustion with air and cleaning with water, followed by circulation through a catalyst preparation step.

The monoalkenyl aromatic hydrocarbon compound obtained by the process of the present invention is useful as the starting intermediate material for various organic compounds typified by high molecular monomers and pharmaceutical preparations. As an example, 5-(o-tolyl)-2-pentene that is produced from o-xylene and 1,3-butadiene can be converted into industrially useful 2,6-naphthalene-dicarboxylic acid by ring closure followed by dehydrogenation, isomerization and oxidation.

The catalyst prepared by the process according to the present invention, even if prepared at a relatively low temperature provided that it is not lower than the melting point of metallic sodium, is given a sufficiently high activity and also is highly active in the side-chain alkenylation reaction of an aromatic hydrocarbon compound with the conjugated diene. Furthermore, even a small usage of the catalyst is effective for producing the monoalkenyl aromatic hydrocarbon compound in high yield and high selectivity, thus facilitating the handling of itself.

The process according to the present invention is capable of producing a monoalkenyl aromatic hydrocarbon compound having industrial availability from an aromatic hydrocarbon compound and a conjugated diene in high yield at a low cost with enhanced safety, thus rendering itself extremely significant from the industrial viewpoint.

In the following, the present invention will be described in more detail with reference to the examples, but shall not be limited thereto.

EXAMPLE 1

To aqueous solution of 5.0 g of potassium hydroxide was added 30 g of zirconium oxide powder (reagent grade, produced by Nakarai Tex Co., Ltd.) to impregnate the powder with the solution under stirring at 50° C. for one (1) hour. Water was distilled away at 70° C. under reduced pressure and the impregnated powder was dried overnight at 115° C. and then calcined in air at 500° C. Thereafter, 10 g of the zirconium oxide powder containing potassium component was stirred at 180° C. in a nitrogen atmosphere and incorporated with 0.50 g of metallic sodium, followed by stirring at the resulting temperature (180° C.) for 60 min. The powdery catalyst thus obtained was incorporated with 1000 g of o-xylene that had been dehydrated with molecular sieve in a stream of nitrogen with heating to 140° C. Then 70 g of 1,3-butadiene was introduced into the reaction system with vigorous stirring for one (1) hour to carry out the reaction. After cooling the system, the catalyst was deactivated by adding isopropyl alcohol thereto and then the reaction liquid was sampled for analysis by gas chromatography. The reaction results are given in Table 1.

EXAMPLE 2 to 6

The procedure in Example 1 was repeated to prepare the catalysts and carry out the reaction by the use thereof except for alteration in the source of zirconium source, the species of the potassium compound, treatment temperature and treatment time as described in Table 1. The reaction results are given in Table 1.

EXAMPLE 7

To 50 g of zirconium oxide powder (model RC-100, produced by Diichi Kigenso Kagaku Kogyo Co., Ltd.) was added water under stirring to form a paste, which was incorporated with 9.9 g of potassium hydroxide (reagent grade with 85% purity) in the form of solid, followed by kneading for 20 minutes. The resultant mixture was dried overnight at 115° C. and then calcined in air at 500° C. for 3 hours. Thereafter, the calcined mixture was ground into powder in a mortar and heated to 180° C. in a nitrogen atmosphere. To 10 g of the resultant zirconium oxide powder containing potassium component was added 0.50 g of metallic sodium, followed by stirring for 60 minutes at the resulting temperature (180° C.). Using the catalyst thus obtained, the reaction was carried out in the same manner as in Example 1. The reaction results are given in Table 1.

EXAMPLE 8

The procedure in Example 7 was repeated to prepare the catalyst except that 12.4 g of potassium zirconate (reagent grade, produced by Soekawa Rikagaku Co., Ltd.) was used in place of potassium hydroxide, and the reaction was carried out in the same manner as in Example 1. The reaction results are given in Table 1.

EXAMPLE 9

The procedure in Example 1 was repeated to carry out the reaction except that the amount of potassium hydroxide was decreased and sodium hydroxide was added to prepare the catalyst. The reaction results are given in Table 1.

COMPARATIVE EXAMPLE 1

The procedure in Example 1 was repeated to prepare the catalyst and carry out the reaction except that 5.7 g of sodium hydroxide was used in place of potassium hydroxide. The reaction results are given in Table 1.

COMPARATIVE EXAMPLE 2

10 g of potassium carbonate powder that had been calcined at 500° C. was heated to 300° C. in nitrogen, incorporated with 0.50 g of metallic sodium with stirring and further heated at the resulting temperature for 120 min. to prepare the catalyst. After allowing the catalyst to cool, the reaction was performed in the same manner as in Example 1. The reaction results are given in Table 1.

COMPARATIVE EXAMPLE 3

The procedure in Example 1 was repeated to carry out the reaction except that 1.0 g of each of metallic sodium and metallic potassium were used as the catalyst. The reaction results are given in Table 1.

TABLE 1

| | $ZrO_2$ source | K-compound (wt %)*1 | Additive (wt %)*2 | Preparation method and usage of K—$ZrO_2$ mixture (g) | Amount of metallic Na (g) | Treatment temperature (°C.) | Treatment time (min.) | OTP*3 (%) |
|---|---|---|---|---|---|---|---|---|
| Example 1 | $ZrO_2$ | KOH (10) | — | impregnation method 10.0 | 0.50 | 180 | 60 | 82.8 |
| Example 2 | $ZrO_2$ | KOH (10) | — | impregnation method 10.0 | 0.50 | 140 | 120 | 81.9 |
| Example 3 | $ZrO_2$ | $K_2CO_3$ (10) | — | impregnation method 10.0 | 0.50 | 180 | 60 | 80.0 |
| Example 4 | $ZrO_2$ | $KHCO_3$ (10) | — | impregnation method 10.0 | 0.50 | 180 | 60 | 80.8 |
| Example 5 | $ZrO_2 \cdot xH_2O$ | KOH (10) | — | impregnation method 10.0 | 0.50 | 180 | 60 | 82.3 |
| Example 6 | $ZrCO_3$ $ZrO_2 \cdot 8H_2O$ | KOH (10) | — | impregnation method 10.0 | 0.50 | 250 | 60 | 79.2 |
| Example 7 | $ZrO_2$ | KOH (10) | — | Kneading method 10.0 | 0.50 | 180 | 60 | 82.5 |
| Example 8 | $ZrO_2$ | $K_2ZrO_3$ (10) | — | Kneading method 10.0 | 0.50 | 180 | 60 | 82.3 |
| Example 9 | $ZrO_2$ | KOH (5.0) | NaOH (5.0) | impregnation method 10.0 | 0.50 | 180 | 60 | 81.9 |
| Comparative Example 1 | $ZrO_2$ | — | NaOH (10) | impregnation method Na-containing $ZrO_2$:10.0 | 0.50 | 180 | 60 | 1.3 |
| Comparative Example 2 | — | $K_2CO_3$ (100) | — | $K_2CO_3$:10.0 | 0.50 | 300 | 120 | 73.0 |
| Comparative Example 3 | — | — | — | — | 1.0 additional metallic K:1.0 g | 180 | 60 | 77.0 |

Remarks:
*1Supported amount of potassium component based on $ZrO_2$ as carrier
*2Supported amount of alkali metal component based on $ZrO_2$ as carrier
*3OTP: 5-(o-tolyl)-2-pentene

EXAMPLE 10

The powdery catalyst that had been prepared in the same manner as in Example 1 was incorporated with 1000 g of toluene that had been dehydrated with molecular sieve, in a stream of nitrogen with heating to 110° C. Subsequently 70 g of 1,3-butadiene was introduced into the reaction system with vigorous stirring for one (1) hour to carry out the reaction. After cooling the system, the catalyst was deactivated by adding isopropyl alcohol thereto and then the reaction liquid was sampled for analysis by gas chromatography- As a result, the objective phenyl-2-pentene was obtained in a yield of 77.2%.

What is claimed is:

1. A process for producing a monoalkenyl aromatic hydrocarbon compound which comprises alkenylating a side chain of an aromatic hydrocarbon compound having at least one hydrogen atom bonded at an α-position of the side chain with a conjugated diene having 4 or 5 carbon atoms in the presence of a catalyst comprising a mixture obtained by heat treating metallic sodium together with a mixture of zirconium oxide and at least one potassium compound selected from the group consisting of potassium hydroxide, potassium carbonate, potassium hydrogen carbonate and potassium zirconate in an inert gas atmosphere.

2. The process according to claim 1 wherein the mixture of the oxide and the potassium compound contains 0.01 to 5 parts by weight of the potassium compound expressed in terms of metallic potassium based on one part by weight of the zirconium oxide.

3. The process according to claim 1 wherein the atomic ratio of the metallic sodium to metallic potassium in the potassium compound is 0.01 to 10.

4. The process according to claim 1 wherein the aromatic hydrocarbon compound having at least one hydrogen atom bonded at an α-position of a side chain is a compound selected from the group consisting of monoalkylbenzene, dialkylbenzene, trialkylbenzene, tetraalkylbenzene, pentaalkylbenzene, hexaalkylbenzene, monoalkylnaphthalene, dialkylnaphthalene, alkyltetrahydronaphthalene and alkylindane.

5. The process according to claim 1 wherein the conjugated diene having 4 or 5 carbon atoms is a diene selected from the group consisting of 1,3-butadiene; 1,3-pentadiene; and isoprene.

6. The process according to claim 1 wherein the molar ratio of the conjugated diene having 4 or 5 carbon atoms to the aromatic hydrocarbon compound having at least one hydrocarbon atom bonded at α-position of a side chain is 0.01 to 1.

7. The process according to claim 1 wherein the catalyst is used in an alkenylation in an amount of at least 0.01% by weight based on the aromatic hydrocarbon compound having at least one hydrocarbon atom bonded at an α-position of a side chain.

8. The process according to claim 2 wherein said aromatic hydrocarbon having at least one hydrogen atom bonded at an α-position of the side chain is a starting material compound selected from the group consisting of monoalkylbenzene, dialkylbenzene, trialkylbenzene, tetraalkylbenzene, pentaalkylbenzene, hexaalkylbenzene, monoalkylnaphthalene, dialkylnaphthalene, alkyltetrahydronaphthalene and alkylindane;

the conjugated diene having 4 or 5 carbon atoms is a diene selected from the group consisting of 1,3-butadiene; 1,3-pentadiene; and isoprene; and the molar ratio of the conjugated diene having 4 or 5 carbon atoms to said aromatic hydrocarbon compound is 0.01 to 1.

9. The process according to claim 8 wherein the mixture of the zirconium oxide and the potassium compound contains 0.02 to 2 parts by weight of the potassium compound expressed in terms of metallic potassium based on one part by weight of the zirconium oxide.

10. The process according to claim 9 wherein the process is carried out at a temperature of 50° to 300° C. and a pressure of 0.05 to 50 absolute atmospheric pressure; and the molar ratio of said conjugated diene to said aromatic hydrocarbon compound is 0.03 to 0.5.

11. The process according to claim 10 wherein the temperature is 90° to 200° C. and the pressure is 0.1 to 20 absolute atmospheric pressure.

12. The process according to claim 11 wherein the catalyst is in an amount of 0.01 weight % or more based on the amount of said aromatic hydrocarbon starting material.

13. The process according to claim 11 wherein the catalyst is in an amount of 0.05 weight % or more based on the amount of the aromatic hydrocarbon starting material.

14. The process according to claim 13 wherein said aromatic hydrocarbon starting material is a compound selected from the group consisting of toluene; ethylbenzene; n-propylbenzene; isopropylbenzene; n-butylbenzene; sec-butylbenzene; isobutylbenzene; o-xylene; m-xylene; p-xylene; o-ethyltoluene; m-ethyltoluene; p-ethyltoluene; o-diethylbenzene; m-diethylbenzene; p-diethybenzene; mesitylene; pseduocumene; 1,2,3,5-tetramethylbenzene; 1,2,4,5-tetramethylbenzene; pentamethylenebenzene; hexamethylbenzene; 1-methylnaphthalene; 2-methylnaphthalene; dimethylnaphthalene; tetrahydronaphthalene; and indane.

15. The process according to claim 13 wherein the aromatic hydrocarbon starting material is o-xylene and the conjugated diene is 1,3-butadiene.

* * * * *